United States Patent [19]

Rogers

[11] 4,427,501

[45] Jan. 24, 1984

[54] METHOD OF MANUFACTURE OF ARTIFICIAL TEETH

[76] Inventor: Olbert W. Rogers, 70 Gymea Bay Rd., Gymea, New South Wales 2227, Australia

[21] Appl. No.: 295,258

[22] Filed: Aug. 24, 1981

Related U.S. Application Data

[63] Continuation-in-part of Ser. No. 28,930, Apr. 11, 1979, abandoned, which is a continuation-in-part of Ser. No. 939,055, Sep. 1, 1978, abandoned, which is a continuation of Ser. No. 722,291, Sep. 10, 1976, Pat. No. 4,125,442.

[51] Int. Cl.³ .................................................. A61C 5/08
[52] U.S. Cl. ...................... 204/37 R; 3/1.9; 204/37 T; 204/38 C; 427/2; 427/330; 427/376.4; 427/383.7; 433/202; 433/222
[58] Field of Search ............... 3/1.9; 204/37 R, 37 T, 204/38 B, 38 S, 38 C, 40; 427/2, 330, 376.2, 376.4, 383.7, 405, 406; 433/202, 222, 223

[56] References Cited

U.S. PATENT DOCUMENTS

| | | | |
|---|---|---|---|
| 1,444,436 | 2/1923 | Teeter et al. | 433/223 |
| 1,782,552 | 11/1930 | Supplee | 433/222 |
| 2,569,453 | 10/1951 | Chester et al. | 148/6.17 |
| 2,819,207 | 1/1958 | Shepard | 204/38 |
| 2,980,998 | 4/1961 | Coleman et al. | 433/222 |
| 3,585,064 | 6/1971 | Prosen | 427/374.2 |
| 3,934,348 | 1/1976 | Janjin | 433/223 |
| 4,064,311 | 12/1977 | McLean et al. | 428/434 |

FOREIGN PATENT DOCUMENTS 2309203  11/1976  France .

*Primary Examiner*—Howard S. Williams
*Assistant Examiner*—William Leader
*Attorney, Agent, or Firm*—Hill, Van Santen, Steadman & Simpson

[57] ABSTRACT

A method of providing an improved bond between porcelain and a basis metal selected from gold, platinum, palladium, silver and alloys thereof, comprises depositing on the basis metal a coating of a second metal selected from gold, platinum and palladium, and then depositing on the second metal a thin layer of a third metal selected from iron, tin, zinc, copper, cobalt and indium. Heat is applied to oxidize the third metal and porcelain is fired onto the oxide so formed.

10 Claims, No Drawings

METHOD OF MANUFACTURE OF ARTIFICIAL TEETH

STATUS OF THE APPLICATION

This application is a continuation-in-part of my earlier U.S. pending application Ser. No. 028,930, filed Apr. 11, 1979, now abandoned, which was a continuation-in-part of my U.S. application Ser. No. 939,055, filed Sept. 1, 1978 now abandoned, which was in turn a continuation of my earlier U.S. application Ser. No. 722,291, filed Sept. 10, 1976 now U.S. Pat. No. 4,125,442.

FIELD OF THE INVENTION

This invention relates to the manufacture of a composite metal-porcelain tooth and/or bone reconstruction wherein porcelain is bonded to a basis metal.

BACKGROUND OF THE INVENTION

In my earlier U.S. patent application Ser. No. 570,740, filed on Apr. 23, 1975, I described a method of making a porcelain tooth reconstruction involving the prior manufacture of a thin metal into which porcelain is fused layer by layer to produce a porcelain insert corresponding accurately to a tooth cavity into which it may subsequently be secured adhesively by means of a conventional dnetal cement.

It is an object of the present invention to produce a metal and porcelain tooth reconstruction suitable either for endosseous implantation in bone tissue or for capping an existing tooth stump.

DESCRIPTION OF THE PRIOR ART

Metal/porcelain reconstructions in themselves are not new; however, a serious problem exists in that current techniques for bonding porcelain to metal are generally unreliable and the effectiveness of such bonds is a matter of dispute and concern and is discussed for example by Fraunhofer, *Scientific Aspects of Dental Materials*, Butterworths 1975, at page 316.

Metals used in the production of metal/porcelain reconstructions include gold, platinum, gold alloys and base metals, usually chromium alloys such as nichrome. Current techniques, however, are unable to provide a satisfactory bond between the metal and the porcelain.

SUMMARY OF THE INVENTION

According to the present invention strong and reliable bonding can be obtained between metal and porcelain to permit the manufacture of tooth reconstructions.

In one aspect the present invention provides a method for use in constructing a composite metal-porcelain tooth and/or bone reconstruction wherein porcelain is bonded to a basis metal, the method comprising the steps of:

(1) providing a substrate of the basis metal, the basis metal being selected from gold, platinum, palladium, silver and alloys thereof;
(2) depositing on the substrate a coating of a second metal which is different from the substrate and is selected from gold, platinum and palladium;
(3) surface treating said coating by depositing thereon a thin layer of a third metal selected from iron, tin, zinc, copper, cobalt and indium;
(4) effecting a heat treatment so as to bond said third metal to said second metal coating and to provide on an outer surface of said third metal an oxide layer thereof,
(5) providing a layer of a porcelain paste on said oxide layer, and
(6) effecting a further heat treatment so as to fire said porcelain paste to form a porcelain layer and to bond the porcelain layer to said oxide layer, whereby the bonding strength between said porcelain layer and said second metal coating is augmented by the presence of said oxide layer.

In another aspect, the two heat treatment steps may be carried out to produce the oxide layer and to fire the porcelain in a single heat treatment.

The invention permits the production of tooth reconstructions either
(a) by building up layers of porcelain on the basis metal, or
(b) by bonding a preformed porcelain facing to the basis metal.

Technique (a) is suitable for producing endosseous implants, and also as is technique (b), suitable for producing tooth crowns.

The present invention employs as the basis metal noble or precious metals selected from gold, platinum, palladium and silver, and preferably employs these in the form of alloys. Such alloys are not in themselves novel and have been described, for example, in "Alternatives to gold alloys in Dentistry", Conference Proceedings Jan. 24–26, 1977 published by the U.S. Department of Health, Education and Welfare. The use of alloys is preferred because of their superior physical properties of hardness etc. and for their inexpensiveness.

As has already been mentioned, existing techniques are unable to provide a satisfactory bond between the metal and porcelain. This is partly due to the different thermal coefficients of expansion of the metal and the porcelain. It is an object of the present invention to provide an improved bond between the metal and porcelain and also to provide a chemical rather than a mere mechanical bond.

The second metal coating is selected from gold, platinum, and palladium, and is applied to the basis metal preferably electrolytically and preferably in a thickness between 1 and 20 microns.

Following the deposition of the second metal coating, in order to improve the bond with the porcelain, the coating is surface-treated by deposition of a thin layer of a third metal, preferably electrolytically, selected from iron, tin, zinc, copper, cobalt and indium, so as to form a metal composite.

The metal composite is generally degassed before the application of the porcelain layer. The principal purpose of a degassing step is to remove from the metals (i.e. the basis metal—second metal—third metal composite) any occluded gases, such as hydrogen or oxygen, which may be present. If these occluded gases are not removed prior to firing of a porcelain layer onto the metals, there is a danger that such occluded gas would be evolved during firing of the porcelain and lead to undesirable porosity of the porcelain, particularly at the interface of the porcelain and the third metal (which is usually tin). Such porosity may detract from the bond between the porcelain and the third metal.

The degassing is largely achieved by the application of heat. The extent of degassing may be improved by the additional application of a partial vacuum to remove residual occluded gas.

It is possible to carry out degassing by simply heating the metal composite in air to a high temperature at atmospheric pressure. However, as an alternative where more extensive degassing is required a partial vacuum may also be applied.

The degassing step may be employed to effect the heat treatment whereby the third metal is bonded to the second metal coating. This heat causes the third metal to diffuse into the surface of the second metal. The presence of air during at least the initial stages of the degassing step is also usually sufficient to cause oxidation of the outer surface of the third metal.

It is relatively easy to effect such a heat treatment at relatively low temperatures at atmospheric or subatmospheric pressure. For example, heating a metal composite wherein the third metal is tin at 100° C. in air at atmospheric pressure quickly leads to the formation of a suitable oxide layer in less than 2 minutes. An oxide layer would be formed on the third metal during heat treatment at higher temperatures and atmospheric air pressure in a matter of seconds after introduction of the metal composite into a furnace.

To the metal composite thus formed, porcelain may now be bonded. The method of bonding porcelain will depend upon the reconstruction required and whether a preformed porcelain facing is to be employed or whether the complete porcelain facing is to be built up in layers on the metal composite.

The presence of the third metal oxide greatly improves wetting of the composite by the applied porcelain, so that the fired porcelain layer accurately follows the the irregular (when viewed under a microscope) surface contours of the metal surface and an excellent bond is produced.

The use of preformed porcelain facings would of course have obvious economic advantages since a wide range of such facings of various shapes and sizes could be mass-produced very cheaply; however, a problem arises in adapting mass-produced porcelain pieces to the infinite variety of contours and colours encountered when treating the teeth of different patients.

The present invention overcomes this difficulty and permits accurate reconstructions using preformed porcelain pieces to be produced corresponding with precision to a tooth to be treated.

This aspect of the present invention is particularly adapted to the manufacture of reconstructions in the form of crowns or caps comprising a metal "thimble" adapted to fit over a tooth stump, to the front of which "thimble" a porcelain facing is attached so that when fixed in the patient's mouth only the porcelain facing is visible.

Thus a model of a tooth stump to be treated is prepared in conventional manner, for example from a plaster material commonly referred to as "artificial stone".

A porcelain facing of the desired colour shade and approximating to the frontal contours of the tooth stump model is then selected, and the rear of such facing is ground to conform reasonably closely to the front surface of the model. It will be appreciated that although by grinding the facing in this way a good approximation of the frontal contours of the model can be achieved, it is virtually impossible to produce a contour sufficiently accurate to permit such facing to be affixed satisfactorily to the model, and certainly it is impossible to do so economically.

The model is then waxed and the porcelain facing is stuck onto the front of the model and is retained in position by means of the wax. In a preferred embodiment a thin metal or other "spacer" is located to provide space for a coating of porcelain material to be applied subsequently as hereinafter described.

By means of the "lost wax" principle, a metal "thimble" is then cast from the basis metal. The thimble so produced will accurately fit over the tooth stump in the patient's mouth and can therefore ultimately be cemented over such stump in the usual way.

The porcelain facing is now bonded to the metal thimble as hereinafter described; it will be appreciated that the facing cannot be merely cemented to the thimble as a quite inadequate bond is thereby achieved.

Thus, the thimble metal composite is pretreated by the methods described hereinbefore. To the front of the thimble thus treated, a layer of porcelain paste is applied to which the porcelain facing is applied. The assembly is then fired to bond the facing and the thimble firmly together.

The technique described permits the formation of a high quality bond between the thimble and the porcelain facing not hitherto possible, as well as permitting the use of mass-produced porcelain facings, either glazed or unglazed, the bond achieved with the latter after vitrification being even better. The use of a platinum deposit rather than a gold deposit also permits the use of the harder high-fusion porcelain.

The deposited layer of said second metal on the basis metal appears to act as a "buffer" zone between the basis metal and the porcelain, which zone absorbs the stresses caused by differences in the coefficients of thermal expansion between the basis metal and the porcelain as it cools from the firing temperature to ambient temperature. In addition it acts as a protective layer preventing the migration of metal ions from the basis metal to the porcelain, which particularly in the case of silver could cause discoloration of the porcelain and also embrittlement of the porcelain.

Preferably substantially pure metals are employed as second metal for deposition on the basis metal. However, small quantities of other metals may be present provided that the coating is sufficiently different from the basis metal to allow for the stress relief mentioned above. Indeed most commercial electroplating solutions will contain traces of other metal ions, such as nickel, indium or cesium, as "brighteners" and grain refiners.

In addition the surface treatment with the third metal results in the formation of oxides during the firing procedure which forms a strong chemical bond with the porcelain.

DETAILED DESCRIPTION OF PREFERRED EMBODIMENTS

The invention will now be illustrated with specific reference to the following Examples:

EXAMPLE 1

A gold inlay alloy (Matthew Garret 101, alloy-precious metal content 96.1%—M.P. 1001° C.) was selected for comparative evaluation of (i) direct ceramic bonding and (ii) bonding after surface treatment according to the invention as follows.

The alloy was in the form of a rolled sheet 15 mm. square and 0.4 mm. thick. After cleaning ultrasonically and washing in distilled water a layer of pure gold was deposited thereon electrolytically using an electrolyte having the following formula:

Potassium gold cyanide: 14.1 g.

Potassium cyanide: 18.3 g.
Potassium carbonate: 14.1 g.
Boric acid: 11.4 g.
Distilled water to 1 liter A current density of 3.2 amp/dm$^2$ was used for 15 minutes at a temperature of 65° C. and an agitation rate of 7 liters per second.

The surface of the electrodeposited gold was rinsed and then flash-plated with tin to provide a suitable sensitised surface for chemical bonding between the metal and ceramic. The tin electrolyte had the following formula:

Potassium stannate: 100. g.
Potassium Hydroxide: 15. g.
Distilled water to 1 liter A current density of 3-5 amp./dm$^2$ was used for 15 seconds at an operating temperature of 65° C. so as to produce an alloy-gold-tin composite.

A feldspar based low temperature maturation porcelain (Vita VMK 68. Vita Zahnfabrik, Sackingen, Germany) was then fired onto both the surface of the gold alloy specimen (i) and the specimen (ii) prepared by the electrodeposition procedures described above, using a vacuum furnace.

The firing cycle comprised:
(a) degassing of specimens by heat treatment for 7 minutes at 955° C. in air at atmospheric pressure.
(b) 2 layers of opaque porcelain were applied-each fired at 905° C. under vacuum.
(c) 2 bakes of body porcelain we applied and each fired at 845° C. under vacuum.

Improved bonding occurred between the porcelain and gold in the treated specimen. The non-treated gold alloy showed a greenish hue through both the opaque porcelain and the body porcelain; this discoloration would render the porcelain quite unacceptable for vital, aesthetic restorative procedures.

EXAMPLE 2

The procedure of Example 1 was repeated to produce an alloy-gold-tin composite as before. A Vita Vacumat F furnace was used to degas the metal composite. The furnace was initially heated to 650° C. and contained air at atmospheric pressure. The metal composite was inserted into the furnace and the furnace closed. Vacuum was then applied and the pressure of air inside the furnace gradually fell from atmospheric pressure to the minimum pressure (normally a few millibars) over a period of around 3 minutes. Thus during this period a substantial quantity of air (and thus oxygen) was present. The temperature was increased after closure of the furnace at a nominal rate of 60° C. per minute until a maximum temperature of 930° C. was reached. Atmospheric pressure was restored before the heat treated degassed metal composite was withdrawn.

The degassed metal composite was then coated with porcelain paste and fired.

EXAMPLE 3

The procedure of Example 3 was repeated to produce an alloy-gold-tin composite as before.

The composite was then degassed in an Ivoclar Programat furnace was used. The cycle was generally as described in Example 2 except that
(1) the metal composite was inserted and the vacuum applied at 420° C.
(2) the final temperature was 920° C. and
(3) the temperature was maintained at 920° C. for about one minute before cooling.

Again, a period of around 3 minutes elapsed before minimum air pressure was reached—during which time a partial pressure of oxygen was present.

The degassed metal composite was then coated with porcelain paste and fired.

EXAMPLE 4

The procedure of Example 1 was repeated to produce an alloy-gold-tin composite as before.

In view of the ease of oxidation of the third metal (e.g. tin), if no degassing step is deemed necessary in a particular instance, it is quite feasible to combine the heat treatment step with the porcelain firing step.

To the metal composite porcelain paste was applied and the assembly fired. In the first few seconds at the high firing temperature the oxide layer is formed on the third metal. Subsequently at higher temperatures the porcelain becomes fired and bonds well to the third metal oxide layer. The third metal oxide layer is thus always formed before the porcelain is fired.

In essence, the heat treatment step is accomplished very quickly after the metal composite (with or without porcelain paste coating) is introduced into the furnace for the first time in the presence of even a relatively small amount of oxygen.

STRENGTH TESTS

Tests were carried out to demonstrate the improved bonding of porcelain to gold or platinum i.e. the second metal which may be brought about by the use of an intermediate layer of tin i.e. the third metal. For the sake of the tests, the second metal was not provided on a substrate of a basis metal since this unduly complicates the test procedure. However, the results obtained are unaffected since there is in general no problem in achieving a good bond between the gold or platinum (i.e. the "second metal") and the basis metal. The results are therefore representative of results to be obtained by carrying out the method of the present invention.

Porcelain discs were prepared using a method suggested by McLean[1] and comprising the following steps:
(a) Electroplate a stone former with a layer of gold or platinum. The stone former is made conductive by the application of a conventional coat of silver metallising paint.
(b) Remove the stone to leave a thimble of gold or platinum.
(c) Tin plate the thimble electrolytically.
(d) Degas the tin-plated thimble by heat treatment at 900° C. in vacuo so as to diffuse the tin into the gold or platinum and produce an outer layer of tin oxide.
(e) Apply an opaque porcelain layer over the tin oxide layer and fire at 900° C.
(f) Apply a body porcelain layer onto the fired opaque porcelain and fire at 900° C.

The thimble is trimmed to produce a disc.

Discs of porcelain 15 mm in diameter were prepared by firing onto various surfaces:
(i) platinum
(ii) tinned platinum
(iii) tinned electroformed gold matrix (EGM)

Vita VMK 68 porcelain was used and fired in the conventional manner. The typical disc thickness was 2.0 mm.

Strength tests were carried out on the prepared porcelain discs by the Australian Dental Standards Laboratory.

The discs were tested to failure in a Shimodyne load cell testing machine by centre loading with a 6 mm diameter spherical indenter while resting on a circular (12 mm diameter) knife edge support.

From Timoshenko[2], the maximum tensile strength on the disc may be calculated.

$$6\,max = \frac{P}{h^2}\left[1 = v)\left(0.485]\ln\frac{a}{h} + 0.52\right) + 0.48\right]$$

where
  h = thickness
  2a = diameter a = 6
  v = Poisson's ratio = 0.23
  P = load at fracture

RESULTS

| | BREAKING STRESS N/mm² | | |
|---|---|---|---|
| | Platinum | Tinned Platinum | EGM Technique |
| Range | 33.3–49.1 | 18.7–79.9 | 41.4–103.8 |
| Mean | 39.5 | 49.5 | 74.1 |
| Standard Deviation | 4.3 | 18.1 | 21.2 |

CONCLUSION

Although the 80% increase in strength due to the use of tinned platinum claimed by McLean could not be substantiated by the present tests here nevertheless was an increase of 25%. However, the use of the EGM technique of the present invention caused an effective increase in porcelain strength of the order of 88%. This was presumably due to the absence of micropores at the interface between the porcelain and the metal.

REFERENCES

[1] Seed, I. R., McLean, J. N. and Hoty, P. "The Strengthening of Aluminous Porcelain with Bonded Platinum Foils". J. Dent. Res. vol. 56, no. 9, September 1977.
[2] Timoshenko, S. and Woinowsky-Kreiger, S. Theory of Plates and Shells. New York: McGraw-Hill, 1959.

I claim:

1. A method for use in constructing a composite metal-porcelain tooth and/or bone reconstruction wherein porcelain is bonded to a basis metal, the method comprising the steps of:
   (1) providing a substrate of the basis metal, the basis metal being selected from gold, platinum, palladium, silver and alloys thereof;
   (2) depositing on the substrate a coating of a second metal which is different from the substrate and is selected from gold, platinum and palladium;
   (3) surface treating said coating by depositing thereon a thin layer of a third metal selected from iron, tin, zinc, copper, cobalt and indium;
   (4) effecting a heat treatment so as to bond said third metal to said second metal coating and to provide on an outer surface of said third metal an oxide layer thereof,
   (5) providing a layer of a porcelain paste on said oxide layer, and
   (6) effecting a further heat treatment so as to fire said porcelain paste to form a porcelain layer and to bond the porcelain layer to said oxide layer, whereby the bonding strength between said porcelain layer and said second metal coating is augmented by the presence of said oxide layer.

2. A method for use in constructing a composite metal-porcelain tooth and/or bone reconstruction wherein porcelain is bonded to a basis metal, the method comprising the steps of:
   (1) providing a substrate of the basis metal, the basis metal being selected from gold, platinum, palladium, silver and alloys thereof;
   (2) depositing on the substrate a coating of a second metal which is different from the substrate and is selected from gold, platinum and palladium;
   (3) surface treating said coating by depositing thereon a thin layer of a third metal selected from iron, tin, zinc, copper, cobalt and indium;
   (4) providing a layer of a porcelain paste on said third metal layer,
   (5) effecting a heat treatment so as to
      (i) bond said third metal to said second metal coating and to provide on an outer surface of said third metal an oxide layer thereof, and
      (ii) fire said porcelain paste to form a porcelain layer and to bond the porcelain layer to said oxide layer, whereby the bonding strength between said porcelain layer and said second metal coating is augmented by the presence of said oxide layer.

3. A method according to either one of claims 1 or 2, wherein the coating of said second metal is deposited electrolytically on to the basis metal to a thickness of between 1 and 20 microns.

4. A method according to either one of claims 1 or 2, wherein the third metal layer is formed by electrolytically depositing a thin layer of said third metal.

5. A method according to either one of claims 1 or 2, wherein a preformed porcelain facing is applied to the porcelain paste.

6. A method according to either one of claims 1 or 2, wherein the porcelain is built up layer by layer.

7. A method for use in constructing a composite metal-porcelain reconstruction wherein porcelain is bonded to a basis metal, the method comprising the steps of:
   (1) providing a substrate of the basis metal, the basis metal being selected from gold, platinum, palladium, silver and alloys thereof;
   (2) depositing on the substrate a coating of a second metal which is different from the substrate and is selected from gold, platinum and palladium;
   (3) surface treating said coating by depositing thereon a thin layer of a third metal selected from iron, tin, zinc, copper, cobalt and indium;
   (4) effecting a heat treatment so as to bond said third metal to said second metal coating and to provide on an outer surface of said third metal an oxide layer thereof,
   (5) providing a layer of a porcelain paste on said oxide layer, and
   (6) effecting a further heat treatment so as to fire said porcelain paste to form a porcelain layer and to bond the porcelain layer to said oxide layer, whereby the bonding strength between said porcelain layer and said second metal coating is augmented by the presence of said oxide layer.

8. A method for use in constructing a composite metal-porcelain reconstruction wherein porcelain is bonded to a basis metal, the method comprising the steps of:

(1) providing a substrate of the basis metal, the basis metal being selected from gold, platinum, palladium, silver and alloys thereof;

(2) depositing on the substrate a coating of a second metal which is different from the substrate and is selected from gold, platinum and palladium;

(3) surface treating said coating by depositing thereon a thin layer of a third metal selected from iron, tin, zinc, copper, cobalt and indium;

(4) providing a layer of a porcelain paste on said third metal layer, (5) effecting a heat treatment so as to (i) bond said third metal to said second metal coating and to provide on an outer surface of said third metal an oxide layer thereof, and (ii) fire said porcelain paste to form a porcelain layer and to bond the porcelain layer to said oxide layer, whereby the bonding strength between said porcelain layer and said second metal coating is augmented by the presence of said oxide layer.

9. A method according to either one of claims 7 or 8, wherein the coating of said second metal is deposited electrolytically on to the basis metal to a thickness of between 1 and 20 microns.

10. A method according to either one of claims 7 or 8, wherein the third metal layer is formed by electrolytically depositing a thin layer of said third metal.

* * * * *